(12) United States Patent
Mehlberg (10) Patent No.: US 9,834,495 B2
(45) Date of Patent: Dec. 5, 2017

(54) EXOTHERM, CONVERSION AND SELECTIVITY MANAGEMENT FOR OLIGOMERIZATION PROCESS

(71) Applicant: UOP LLC, Des Plaines, IL (US)

(72) Inventor: Robert L. Mehlberg, Wheaton, IL (US)

(73) Assignee: UOP LLC, Des Plaines, IL (US)

( * ) Notice: Subject to any disclaimer, the term of this patent is extended or adjusted under 35 U.S.C. 154(b) by 169 days.

(21) Appl. No.: 14/316,178

(22) Filed: Jun. 26, 2014

(65) Prior Publication Data

US 2015/0376083 A1    Dec. 31, 2015

(51) Int. Cl.

| | |
|---|---|
| C07C 2/58 | (2006.01) |
| C07C 5/03 | (2006.01) |
| C07C 5/32 | (2006.01) |
| C07C 2/08 | (2006.01) |
| C07C 5/333 | (2006.01) |
| C10G 45/02 | (2006.01) |
| C10G 50/00 | (2006.01) |
| C10G 69/12 | (2006.01) |

(52) U.S. Cl.
CPC ............. *C07C 5/333* (2013.01); *C10G 45/02* (2013.01); *C10G 50/00* (2013.01); *C10G 69/126* (2013.01); *C10G 2400/02* (2013.01); *C10G 2400/04* (2013.01); *C10G 2400/08* (2013.01)

(58) Field of Classification Search
CPC .... C07C 2/58; C07C 5/03; C07C 5/32; C07C 2/08
See application file for complete search history.

(56) References Cited

U.S. PATENT DOCUMENTS

| | | | |
|---|---|---|---|
| 3,644,564 A | | 2/1972 | van Zwet |
| 3,697,617 A | | 10/1972 | Yoo |
| 4,720,600 A | * | 1/1988 | Beech, Jr. ................. C07C 2/12 |
| | | | 585/315 |
| 5,811,608 A | | 9/1998 | Stine et al. |
| 5,847,252 A | | 12/1998 | Stine et al. |
| 5,856,604 A | | 1/1999 | Stine et al. |
| 6,025,533 A | * | 2/2000 | Vora ..................... C10G 69/126 |
| | | | 585/315 |
| 2006/0199985 A1 | * | 9/2006 | Kuechler ............... C10G 50/00 |
| | | | 585/1 |
| 2010/0331591 A1 | | 12/2010 | Brown et al. |
| 2012/0142989 A1 | * | 6/2012 | Jaber ......................... C07C 2/36 |
| | | | 585/532 |

OTHER PUBLICATIONS

PCT International Search Report and Written Opinion dated Sep. 28, 2015, for PCT/US2015/034811.

\* cited by examiner

*Primary Examiner* — In Suk Bullock
*Assistant Examiner* — Youngsul Jeong (57) ABSTRACT

A process is presented for the control of the exotherm from an oligomerization process. The oligomerization process is for the conversion of C3 and C4 olefins to distillate. The process includes controlling the extent of the reaction to limit temperature rise, and recycle of a portion of the reactor effluent stream for dilution of the C3 and C4 olefins passed to the oligomerization reactors, and for separating out the product distillate.

18 Claims, 4 Drawing Sheets

EXOTHERM, CONVERSION AND SELECTIVITY MANAGEMENT FOR OLIGOMERIZATION PROCESS

FIELD OF THE INVENTION

The present invention relates to the production of liquid fuels from light hydrocarbon feedstocks. In particular, the process is for the conversion of propane into fuels such as gasoline and distillate.

BACKGROUND

The oligomerization of olefins is known. Oligomerization is carried out by reacting olefinic hydrocarbons over catalysts to obtain various oligomers. Oligomerization is often applied to the process of forming dimers, trimers, and tetramers from monomers, and also can cover polymerization processes.

One oligomerization process is described in U.S. Pat. No. 3,697,617 and involves the use of a catalyst that comprises a complex of nickel in an electron donor ligand. The complex deposited on a solid support of an acidic material such as silica-alumina. The polymerization of an olefin is described in U.S. Pat. No. 3,644,564, using a nickel compound catalyst. U.S. Pat. No. 3,644,564 describes the oligomerization of ethylene. Other patents which describe catalysts for the oligomerization or polymerization of olefins.

While there are catalysts and processes for the oligomerization of olefins, there is a need for increased products that result from oligomerization of olefins, and the control of the process for generating liquid fuels and other liquids from light olefins still presents problems that need to be solved.

SUMMARY

A first embodiment of the invention is a process for managing heat release, conversion and selectivity in a dehydrogenation and oligomerization process, comprising passing a first stream comprising propane or isobutane to a dehydrogenation reactor to generate a dehydrogenation stream comprising propylene or isobutene, operated to produce less than 50% conversion of the propane or isobutane; passing the dehydrogenation stream to a first oligomerization reactor to generate a first oligomerization effluent stream; passing a first portion of the first oligomerization stream to the first oligomerization reactor; passing a second portion of the first oligomerization effluent stream to a second oligomerization reactor to generate a second oligomerization effluent stream; and passing the second oligomerization effluent stream to a distillate splitter. An embodiment of the invention is one, any or all of prior embodiments in this paragraph up through the first embodiment in this paragraph wherein the first oligomerization reactor is operated to perform a conversion of at least 90% of propylene or isobutene to heavier hydrocarbons; passing the first oligomerization effluent stream to a stabilizer to generate a stabilizer overhead stream comprising C4s and lighter gases, and a stabilizer bottoms stream comprising C6+ hydrocarbons; passing a first portion of the stabilizer bottoms stream to the second oligomerization unit; and passing a second portion of the stabilizer bottoms stream to the first oligomerization unit. An embodiment of the invention is one, any or all of prior embodiments in this paragraph up through the first embodiment in this paragraph wherein the dehydrogenation reactor is operated to convert between 20 and 40% of the propane or isobutane in the first stream to propylene or isobutene. An embodiment of the invention is one, any or all of prior embodiments in this paragraph up through the first embodiment in this paragraph further comprising passing the second oligomerization effluent stream to a complete saturation unit to generate an effluent stream with reduced olefin content; and passing the effluent stream with reduce olefin content to the distillate splitter to generate an overhead stream for passing to a gasoline blending pool or recycle for conversion of the gasoline range olefins to additional distillate, and a distillate bottoms stream. An embodiment of the invention is one, any or all of prior embodiments in this paragraph up through the first embodiment in this paragraph further comprising passing the second oligomerization effluent stream to a complete saturation unit to generate an effluent stream with reduced olefin content. An embodiment of the invention is one, any or all of prior embodiments in this paragraph up through the first embodiment in this paragraph further comprising passing a portion of the distillate bottoms stream to the second oligomerization reactor. An embodiment of the invention is one, any or all of prior embodiments in this paragraph up through the first embodiment in this paragraph further comprising passing the dehydrogenation stream to an aromatics removal unit to generate an aromatics free dehydrogenation stream; and passing the aromatics free dehydrogenation stream to the first oligomerization reactor. An embodiment of the invention is one, any or all of prior embodiments in this paragraph up through the first embodiment in this paragraph further comprising passing the dehydrogenation stream to a sulfur removal unit to generate a sulfur free dehydrogenation stream; and passing the sulfur free dehydrogenation stream to the first oligomerization reactor.

A second embodiment of the invention is a process for the production of distillate from light paraffins, comprising passing a first stream comprising light paraffins to a dehydrogenation zone to generate a second stream comprising light olefins; passing the second stream to a first oligomerization reactor to generate a third stream comprising oligomers; cooling the third stream to generate a cooled third stream; passing a first portion of the cooled third stream to the first oligomerization reactor, operated at reaction conditions sufficient to achieve oligomerization of the light olefin to less than 70%; passing a second portion of the cooled third stream to a second oligomerization reactor to generate a distillate process stream, operated at reaction conditions sufficient to achieve oligomerization of the light olefin to at least 90%; and recovering distillate from the distillate process stream. An embodiment of the invention is one, any or all of prior embodiments in this paragraph up through the second embodiment in this paragraph wherein the first stream comprising light paraffins comprises propane or isobutane. An embodiment of the invention is one, any or all of prior embodiments in this paragraph up through the second embodiment in this paragraph wherein the second stream comprising olefins comprises propylene or isobutene. An embodiment of the invention is one, any or all of prior embodiments in this paragraph up through the second embodiment in this paragraph wherein the first portion of the first oligomerization stream is sized to limit the temperature rise in the reactor to less than 60° F. (3° C.). An embodiment of the invention is one, any or all of prior embodiments in this paragraph up through the second embodiment in this paragraph further comprising passing the distillate process stream to a stabilizer to generate an overhead stream comprising C3 and lighter hydrocarbons, and a bottoms stream comprising distillate; passing a first portion of the bottoms stream to the second oligomerization reactor; and passing a second portion of the distillate to a distillate splitter to generate a distillate splitter overhead comprising olefinic gasoline, and a distillate splitter bottoms stream comprising distillate. An embodiment of the invention is one, any or all of prior embodiments in this paragraph up through the second embodiment in this paragraph further comprising passing the distillate splitter bottoms stream to a complete saturation unit to generate a saturated distillate bottoms stream; and passing the saturated distillate bottoms stream to a stripper to generate a light ends overhead stream and a distillate product bottoms stream.

A third embodiment of the invention is a process for controlling the heat of reaction in a light paraffins to distillate conversion process, comprising passing a first stream comprising a light paraffin to a dehydrogenation unit to generate a second stream comprising a light olefin; passing the second stream comprising light olefins to a first oligomerization reactor operated at reaction conditions for a conversion of less than 70% of the olefins to heavier hydrocarbons to generate a first oligomerization effluent stream; passing the oligomerization effluent stream to a flash unit to generate a flash vapor stream and a flash liquid stream; passing a first portion of the flash liquid stream to the first oligomerization unit; passing a second portion of the flash liquid stream and the flash vapor stream to a second oligomerization unit to generate a second oligomerization effluent stream; passing the second oligomerization effluent stream to a stabilizer to generate a stabilizer overhead stream and a stabilizer bottoms stream; and passing the stabilizer bottoms stream to a distillate stripper to generate an olefinic gasoline overhead and a distillate stream. An embodiment of the invention is one, any or all of prior embodiments in this paragraph up through the third embodiment in this paragraph further comprising passing a portion of the stabilizer bottoms stream to the second oligomerization reactor. An embodiment of the invention is one, any or all of prior embodiments in this paragraph up through the third embodiment in this paragraph further comprising passing a portion of the olefinic gasoline overhead to the second oligomerization reactor. An embodiment of the invention is one, any or all of prior embodiments in this paragraph up through the third embodiment in this paragraph further comprising passing the second portion of the flash liquid stream to a flash liquid stripper to generate a flash liquid stripper overhead stream comprising C9- hydrocarbons and a flash liquid stripper bottoms stream comprising C10+ hydrocarbons; and passing the flash liquid stripper overhead stream to the second oligomerization reactor. An embodiment of the invention is one, any or all of prior embodiments in this paragraph up through the third embodiment in this paragraph further comprising passing the flash liquid stripper bottoms stream to the distillate stripper.

A fourth embodiment of the invention is a process for controlling the conversion of paraffins to distillate, comprising passing a first stream comprising propane or isobutane to a dehydrogenation unit to generate a second stream comprising propylene or isobutene; passing the second stream to a first oligomerization reactor operated at reaction conditions for a conversion of less than 70% of the olefins to heavier hydrocarbons to generate a first oligomerization effluent stream; cooling the first oligomerization effluent stream to generate a cooled first oligomerization effluent stream; passing a first portion of the cooled first oligomerization effluent stream to the first oligomerization reactor; passing a second portion of the cooled first oligomerization effluent stream to a flash unit to generate a flash vapor stream and a flash liquid stream comprising olefinic distillate; passing a first portion of the flash vapor stream to the first oligomerization reactor; passing a second portion of the flash vapor stream to a second oligomerization reactor to generate a second oligomerization effluent stream; passing the flash liquid stream to a flash liquid stripper to generate a flash liquid stripper overhead stream comprising C9- hydrocarbons and a flash liquid stripper bottoms stream comprising C10+ distillate hydrocarbons; passing the flash liquid stripper overhead stream to the second oligomerization reactor; passing the second oligomerization effluent stream to a stabilizer to generate a stabilizer overhead stream and a stabilizer bottoms stream; and passing the stabilizer bottoms stream to the distillate stripper to generate an olefinic gasoline overhead and a distillate stream.

Other objects, advantages and applications of the present invention will become apparent to those skilled in the art from the following detailed description and drawings.

DETAILED DESCRIPTION

The control of the energy in a chemical reaction process can improve the selectivity of the reaction and the conversion and maximize catalyst life. As a chemical process proceeds, it can be exothermic or endothermic, where the temperature either rises or falls as the reaction proceeds. As the temperature changes, the rate of reaction declines and the yields are decreased. Other aspects of changing temperatures includes shifts in selectivity and/or the relative increase in undesired side reactions. This is important for catalytic reactions as catalysts are often operated at conditions to control selectivity and to minimize adverse reactions. While distillate is a term used in many contexts, within the petroleum refining industry, distillate is a term used to cover aliphatic hydrocarbons, typically in the gasoline, naphtha, diesel or kerosene ranges, and heavy distillates including heavy fuel oils. In the context of this invention, distillate is used to indicate fuels or fuel blending components comprising C9+ hydrocarbons.

The present invention provides a method for controlling the oligomerization reaction of light olefins to produce heavier hydrocarbon products, such as distillate. Oligomerization is an exothermic process, and the exotherm, or heat released the increases the temperature, needs to be controlled for an effective and efficient process. In particular, this is aimed at converting light paraffins such as propane or isobutane to distillate. The process can include the step of separating out unreacted paraffins and olefins from a process stream. For the operation with propane conversion a depropanizer would be used, likewise for an isobutane stream a debutanizer would be used. In the present invention, a stabilizer is used and can mean either a depropanizer or a debutanizer, depending on the feedstock to the process.

Oligomerization is a process for increasing the size of hydrocarbon molecules by combining smaller hydrocarbons. The process is a catalytic process and is operated in a reactor under pressure at elevated temperatures. Oligomerization catalysts include zeolites having TON, MTT, MFI, MEL, AFO, AEL, EUO and FER type structures, solid phosphoric acid catalysts, and mixtures of the different zeolite structures. The catalysts can also include a support and a binder.

The process includes operation of the oligomerization zones at oligomerization reaction conditions, wherein the oligomerization reaction conditions include a reaction temperature between 100° C. to 250° C., and a reaction pressure between 100 kPa to 2000 kPa (absolute).

Figure 1:
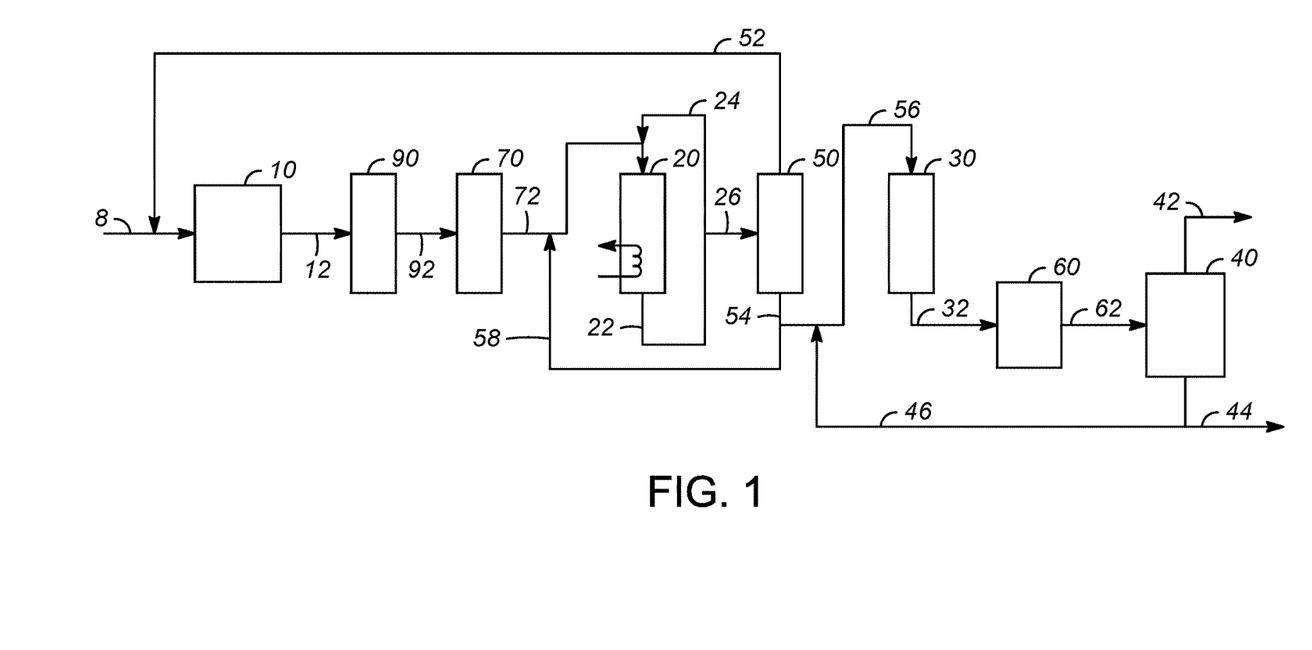
FIG. 1 is a first embodiment of the present invention.

The process, as shown in FIG. 1, includes a two stage reactor for the conversion of a light paraffin process stream into a distillate. A first stream 8, comprising the light paraffin, is passed to a dehydrogenation reactor 10 to generate a dehydrogenation stream 12 comprising an olefin. The reactor 10 is operated at conditions to yield the process stream such that less than 50% of the paraffin is converted to olefin. In a preferred operation, the dehydrogenation reactor is operated for the conversion of paraffins to a level between 20% and 40% conversion, and a more preferred level of about 30% conversion, and with a preferred level of at least 25% conversion. The dehydrogenation stream 12 is passed to a first oligomerization reactor 20 to generate a first oligomerization effluent stream 22. The first oligomerization reactor 20 is operated for a conversion level of propylene to higher hydrocarbons of between 80 and 99%, with a preferred level of conversion between 90 and 95%. The process includes passing a first portion 24 of the first oligomerization stream 22 to the first oligomerization reactor 20. A second portion 26 of the first oligomerization stream 22 is passed to a second oligomerization reactor 30 to generate a second oligomerization effluent stream 32. The second oligomerization stream 32 is passed to a distillate splitter 40.

The process can further include passing the second oligomerization effluent stream 32 to a complete saturation unit 60 to generate an effluent stream 62 with reduced olefin content. The effluent stream 62 is passed to the distillate splitter 40 to generate an overhead stream 42 for passage to a gasoline blending pool, and a distillate bottoms stream 44.

The process can further include passing the dehydrogenation stream 12 to an aromatics removal unit 70 to generate an aromatics free dehydrogenation stream 72. The aromatics free dehydrogenation stream 72 is then passed to the first oligomerization reactor 20. The process can further includes passing the dehydrogenation stream 12 to a sulfur removal unit 90 to remove residual sulfur and generate a sulfur free dehydrogenation stream 92. The sulfur free dehydrogenation stream 92 can then be passed to the first oligomerization reactor 20, or first to the aromatics removal unit 70, in cases where the level of aromatics generated by the dehydrogenation reactor is above a minimum level.

In one embodiment, the process further includes passing the first oligomerization stream 22 to a stabilizer 50 to generate a stabilizer overhead stream 52 comprising light paraffins and olefins, and a stabilizer bottoms stream 54 comprising C6 and heavier hydrocarbons. A first portion of the stabilizer bottoms stream 56 is passed to the second oligomerization unit 30, and a second portion of the stabilizer bottoms stream 58 is passed to the first oligomerization unit 20.

The process can further include passing a portion of the distillate bottoms stream 46 to the second oligomerization reactor 30.

The oligomerization reaction is exothermic and generates heat, such that if operated as an adiabatic process, the temperature will rise about 110° C. for a conversion level of about 90% for a feed containing 30% propene. To manage this heat rise, the recycling of a portion of the process stream effluent 24 can control and reduce the temperature rise. In another alternative, a heat exchanger can be added into the reactor 20 to remove heat as it is generated during the reaction. The heat exchanger can comprise an exchanger that generates steam which can be transferred and used in other processes. One advantage for the heat exchanger is a minimization of reactor volume, and associated volume of catalyst, and reduced pumping and circulation costs, but these reactors tend to be small and costly per unit of reactor volume.

The process is intended to control the heat generated to less than 60° F., or 33.3° C., for a conversion level of 95% of propylene in the oligomerization reactor feed with an effluent recycle. Table 1 shows material balances for a recycle reactor based on 100 kg./hr fresh feed from a dehydrogenation unit. To control the exotherm below 60° F. (33.3° C.) 243 kg/hr of recycle are required for maintaining this limit. Because unconverted propylene and $C_6$-$C_9$ olefins are recycled as well, the reactor $C_3$= conversion per pass is reduced to 85% for an overall conversion of 95% while helping to reduce the reactor volume. But despite the lower conversion per pass of the reactor the higher total reactor flowrate increases the reactor and catalyst volume by 115% relative to the minimum sized reactor without recycle. The recycle reactor also increases the $C_6$-$C_9$ olefin concentrations in the reactor which enhances selectivity to distillate, but it also increases the $C_{10}$+ distillate concentration in the reactor which can increase the molecular weight and 90% distillation point of the product more than is desired.

TABLE 1

Example of reactor temperature rise from adiabatic process with recycle.

| | Fresh feed comp. Kg/hr | Reactor 1 Recycle flows Kg/hr | Reactor 1 feed Kg/hr | Reactor 1 reaction Kg/hr | Reactor 1 effluent Kg/hr | Net Product Kg/hr |
|---|---|---|---|---|---|---|
| C3= | 30 | 3.6 | 33.6 | −28.5 | 5.1 | 1.5 |
| iC4= | 1 | 0.1 | 1.1 | −1.0 | 0.2 | 0.1 |
| C5= | 0 | 0.0 | 0 | 0 | 0.0 | 0.0 |
| C6= to C9= | 0 | 12.4 | 12.4 | 5.1 | 17.5 | 5.1 |
| Aromatic (unreactive) | 0.2 | 0.4 | 0.5 | | 0.5 | 0.2 |
| Dienes (reactive) | 0.1 | 0.1 | 0.2 | | 0.2 | 0.1 |
| Other (reactive) | 0.1 | 0.1 | 0.2 | | 0.2 | 0.1 |
| Other | 1.8 | 4.4 | 6.2 | | 6.2 | 1.8 |
| C3 + iC4 | 67 | 162.7 | 229.6 | | 229.6 | 67.0 |
| Oligomers | 0 | 59.1 | 59.1 | 24.3 | 83.5 | 24.3 |
| Total | 100 | 243.0 | 343.0 | 0 | 343.0 | 100.0 |

Figure 2:
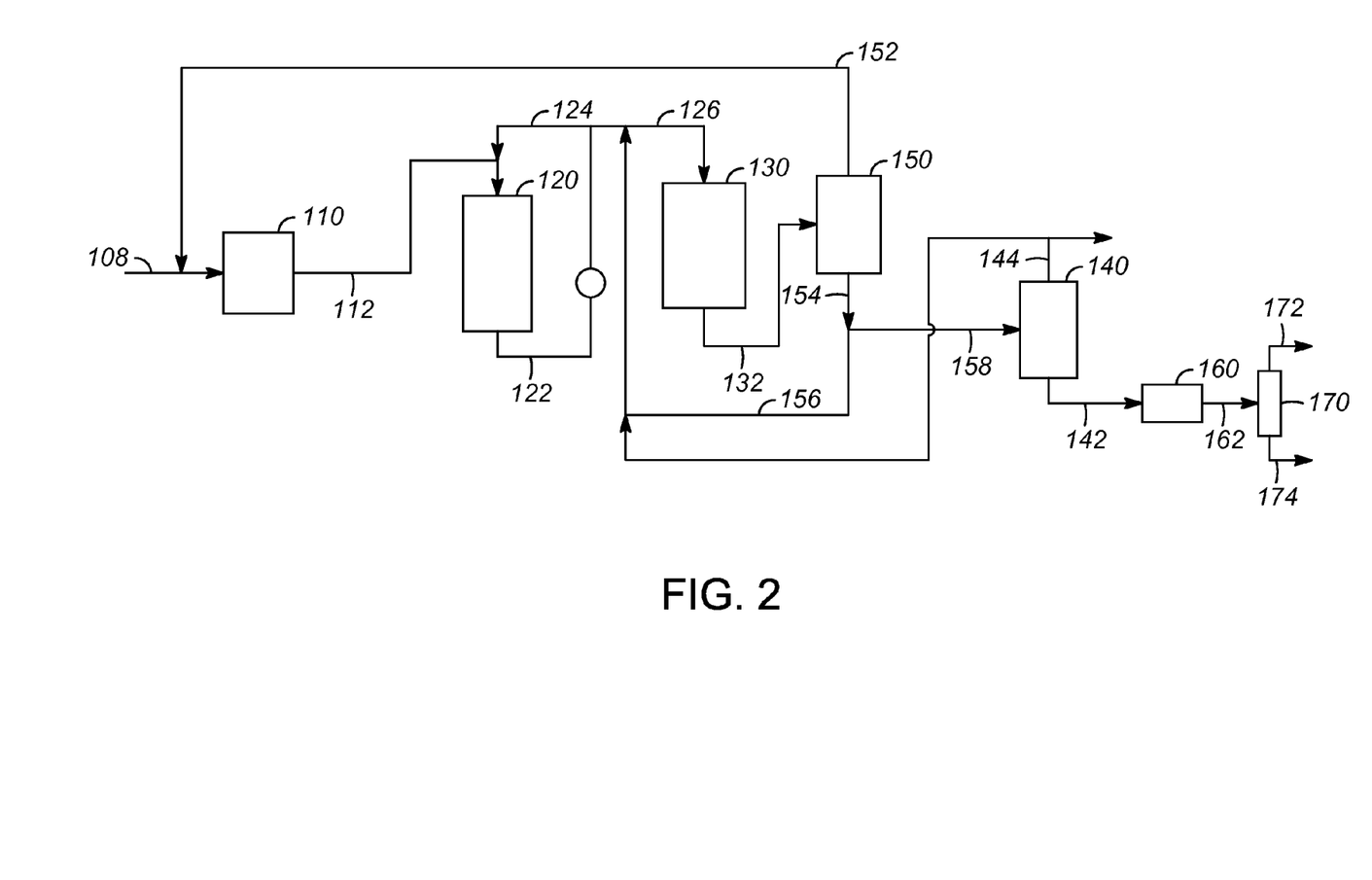
FIG. 2 is a second embodiment of the present invention.

In another embodiment, the process for the production of distillate from light paraffins can be seen in FIG. 2. The term light paraffins is intended to cover C3 and C4 paraffins. A first stream 108 comprising light paraffins is passed to a dehydrogenation zone 110 to generate a second stream 112 of light olefins. The second stream 112 is passed to a first oligomerization reactor 120 to generate a third stream 122 comprising oligomers and unreacted light paraffins and olefins. The third stream is cooled and a first portion 124 of the cooled stream is passed to the first oligomerization reactor 120. The first oligomerization reactor 120 is operated at reaction conditions to achieve oligomerization of the light olefin to a level of less than 70%. A second portion 126 of the cooled third stream is passed to a second oligomerization reactor 130 to generate a distillate process stream 132. The second oligomerization reactor is operate at reaction conditions to continue oligomerizing the light olefins such that at least 90% of the light olefins generated by the dehydrogenation reactor are oligomerized. The distillate process stream 132 is passed to a distillate splitter 140 to generate a distillate product stream 142. This process includes the recycle of hexenes generated in the first oligomerization reactor 120 and present in stream 124 for further oligomerization.

In one embodiment, the light paraffins in the first stream 108 comprises propane, and the dehydrogenation reactor generates the second process stream 112 comprising propane and propylene. In another embodiment, the light paraffins in the first stream 108 comprises isobutane, and the dehydrogenation reactor generates the second process stream 112 comprising isobutane and isobutene.

By limiting the conversion rate in the first oligomerization reactor 120, with recycle of a portion of the first oligomerization stream 122, the temperature rise is limited to less than 60° F., or 33.3° C.

To further control the temperature rise in the first oligomerization reactor 120, the first portion 124 can be split and a part of the first portion is fed to the top of the reactor, and a second part is fed to an intermediate position in the first reactor 120. For control in the second oligomerization reactor 130, a part of the second portion 126 can be fed into the top of the reactor with a second part fed to an intermediate position in the second reactor 130.

The process can further include that the first portion 124 of the first oligomerization stream is of sufficient size to dilute the light olefins concentration in the feed to the first oligomerization reactor 120 to a level of less than 50% of the concentration of the second stream 112 from the dehydrogenation zone 110.

The process can further include passing the distillate process stream 132 to a stabilizer 150 to generate an overhead stream 152 comprising lighter hydrocarbons and gases, and a bottoms stream 154 comprising distillate. A first portion 156 of the bottoms stream 154 is passed to the second oligomerization reactor 130, and a second portion 158 of the bottoms stream 154 is passed to the distillate splitter 140 to generate the distillate splitter overhead 144 comprising an olefinic gasoline, and the distillate splitter bottoms stream 142 comprising distillate. The process can further include passing the distillate splitter bottoms stream 142 to a complete saturation unit 160 to generate a saturated distillate bottoms stream 162. The saturated distillate bottoms stream 162 is passed to a stripper 170 to remove light ends generated in the saturation process, or to generate a light ends overhead stream 172 and a distillate product bottoms stream 174.

By limiting the extent of the oligomerization reactor, the amount of recycle is reduced and the amount of temperature rise can be controlled. In this embodiment, a smaller portion of the olefins from the dehydrogenation reactor 120 are oligomerized, operated to allow for less than 70% conversion, in the first oligomerization reactor, with the remaining conversion performed in the second reactor 130 to bring the overall conversion to the 90-95% level.

Table 2a,b shows the material balances for a 2-stage adiabatic process such as that shown in FIG. 2 based upon 100 kg/hr of olefins in stream 112. The first oligomerization reactor, 120, is operated at lower conversion (about 45%) with cooled effluent recycle, 124, to limit the exotherm to 60° F., 33.3° C. By operating at lower conversion the recycle requirement of stream 124 is reduced to 138 kg/hr. Furthermore it lowers the $C_3=$ concentration in the $2^{nd}$ oligomerization reactor feed, 130, so that it can be operated at 85% conversion without recycle is required to maintain the exotherm under 60° F. because the propylene concentration low enough.

For a $1^{st}$ order reaction at the same temperature this 2-stage recycle scheme at lower conversion per stage surprisingly reduces the overall reactor volume to only 12% higher than the minimum reactor size for 95% conversion of the olefins in stream 112.

TABLE 2a

2-Stage Adiabatic Oligomerization Material Balances

| | Fresh feed comp. Kg/hr | Reactor 1 Recycle flows Kg/hr | Reactor 1 feed Kg/hr | Reactor 1 reaction Kg/hr | Reactor 1 effluent Kg/hr |
|---|---|---|---|---|---|
| C3= | 30 | 14.44 | 44.44 | −20.1 | 24.34 |
| iC4= | 1 | 0.15 | 1.15 | −0.9 | 0.25 |
| C5= | 0 | 0.0 | 0 | 0 | 0.0 |
| C6= to C9= | 0 | 6.39 | 6.39 | 4.38 | 10.77 |
| Aromatic (unreactive) | 0.15 | 0 | 0.15 | | 0.15 |
| Dienes (reactive) | 0.05 | 0 | 0.05 | −0.05 | 0.0 |
| Other (reactive) | 0.05 | 0 | 0.05 | −0.05 | 0.0 |
| Other | 1.8 | 0 | 1.8 | | 1.8 |
| C3 + iC4 | 66.95 | 97.64 | 164.59 | | 164.59 |
| Oligomers | 0 | 24.38 | 24.38 | 16.72 | 41.1 |
| Total | 100 | 143.0 | 243.0 | 0 | 243.0 |

TABLE 2b

2-Stage Adiabatic Oligomerization Material Balances

| | Reactor 2 feed comp. Kg/hr | Reactor 2 Recycle flows Kg/hr | Reactor 2 total feed Kg/hr | Reactor 2 reaction Kg/hr | Reactor 2 effluent Kg/hr | Net Product Kg/hr |
|---|---|---|---|---|---|---|
| C3= | 9.9 | | 9.9 | −8.4 | 1.5 | 1.5 |
| iC4= | 0.1 | | 0.1 | −0.05 | 0.05 | 0.05 |
| C5= | 0 | | 0 | 0 | 0 | 0.0 |
| C6= to C9= | 4.38 | | 4.38 | 1.22 | 5.6 | 5.6 |
| Aromatic (unreactive) | 0.15 | | 0.15 | | 0.15 | 0.15 |
| Dienes (reactive) | 0 | | 0 | 0 | 0 | 0 |
| Other (reactive) | 0 | | 0 | 0 | 0 | 0 |
| Other | 1.8 | | 1.8 | | 1.8 | 1.8 |
| C3 + iC4 | 66.95 | | 66.95 | | 66.95 | 66.95 |
| Oligomers | 16.72 | | 16.72 | 7.23 | 23.95 | 23.95 |
| Total | 100 | | 100.0 | 0 | 100.0 | 100.0 |

Figure 3:
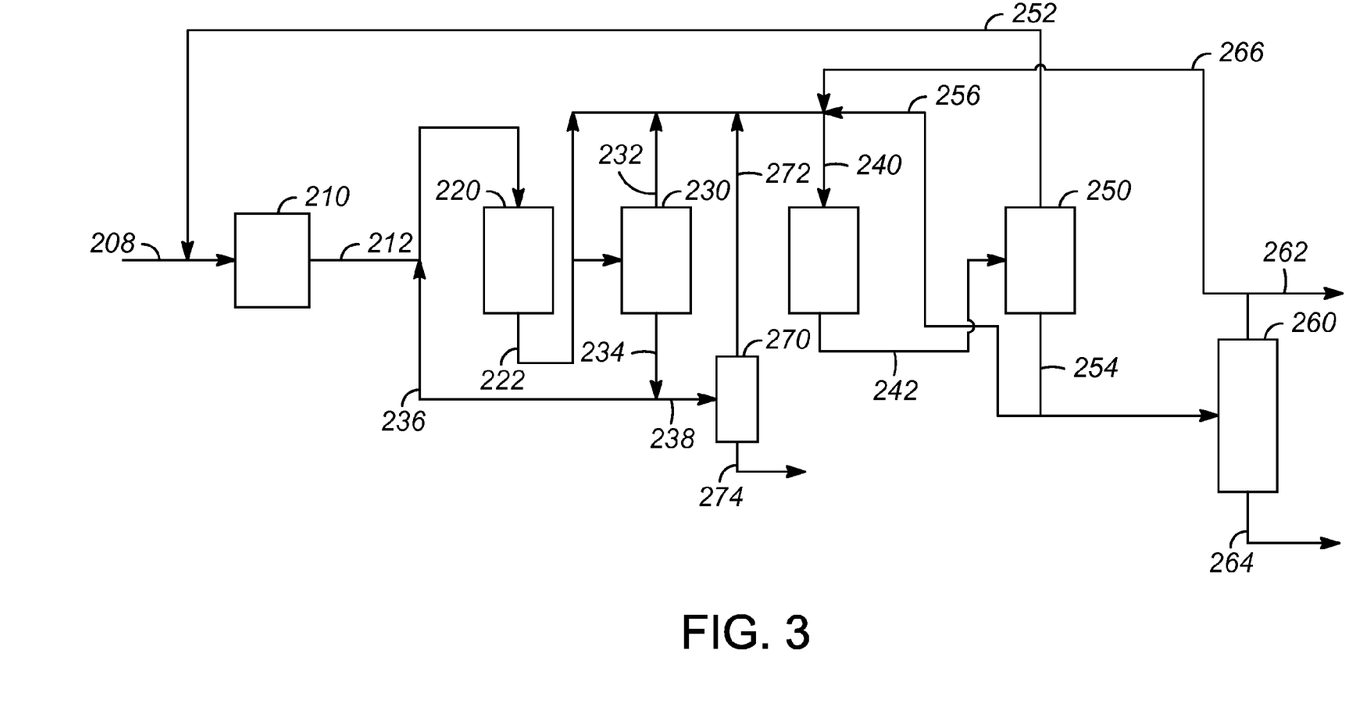
FIG. 3 is a third embodiment of the present invention.

In another embodiment, the process for controlling the heat of reaction in an olefins to distillate conversion process can be seen in FIG. 3. The process is for controlling the heat of reaction, the rate of olefin conversion, distillate selectivity and distillate boiling point distribution in a light paraffins to distillate conversion process.

The process includes passing a first stream 208, comprising a light paraffin to a dehydrogenation unit 210 to generate a second stream 212 comprising a light olefin. The second stream 212 is passed to a first oligomerization reactor 220 operated at reaction conditions for a conversion of less than 70% of the olefins to heavier hydrocarbons, to generate a first oligomerization effluent stream 222. The first oligomerization effluent stream is passed to a flash unit 230 to generate a flash vapor stream 232 and a flash liquid stream 234. A first portion of the flash liquid stream 236 is passed to the first oligomerization unit 220. A second portion of the flash liquid stream 238 and the flash vapor stream 232 are passed to a second oligomerization unit 240 to generate a second oligomerization effluent stream 242. The second oligomerization effluent stream 242 is passed to a stabilizer 250 to generate a stabilizer overhead stream 252 and a stabilizer bottoms stream 254. The stabilizer bottoms stream 254 is passed to a distillate stripper 260 to generate an olefinic gasoline overhead stream 262 and a distillate stream 264.

The process can further include passing a portion of the stabilizer bottoms stream 256 to the second oligomerization reactor 240. In another variation, a portion of the olefinic gasoline overhead stream 266 can be passed to the second oligomerization reactor 240.

In one embodiment, the process further includes passing the second portion of the flash liquid stream 238 to a flash liquid stripper 270 to generate a flash liquid stripper overhead stream 272 comprising C9− hydrocarbons and a flash liquid stripper bottoms stream 274 comprising C10+ hydrocarbons. The flash liquid stripper overhead stream 272 is passed to the second oligomerization reactor 240. The flash liquid stripper bottoms stream 274 comprises distillate, and can be passed to a distillate storage unit. The flash liquid stripper bottoms stream 274 can also be passed to the distillate stripper 260 to remove heavy olefins from the distillate.

Figure 4:
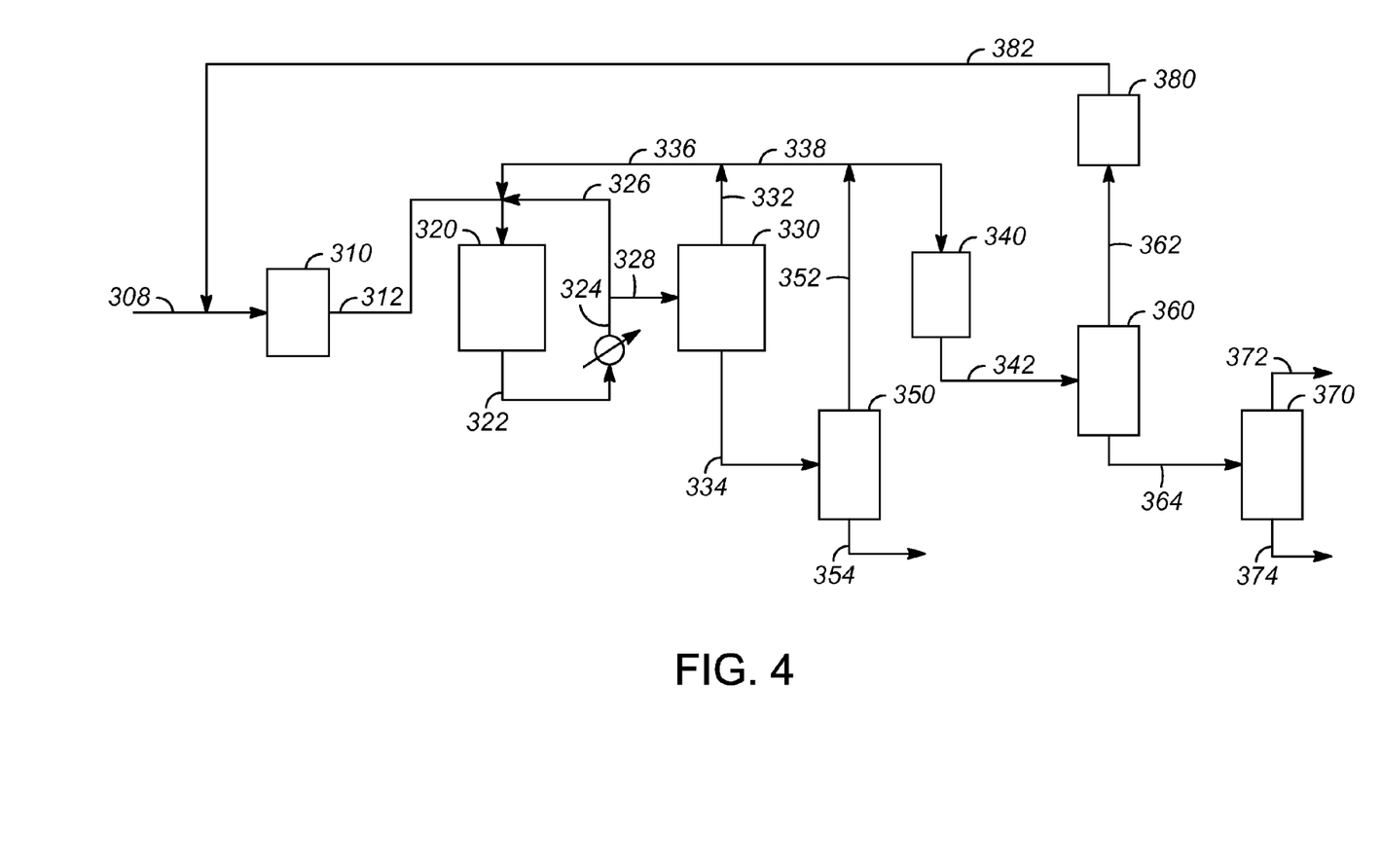
FIG. 4 is a fourth embodiment of the present invention.

In another embodiment, the process is shown as in FIG. 4. The process includes passing a first stream 308 comprising light paraffins of either propane or isobutane to a dehydrogenation unit 310 to generate a second stream 312 comprising olefins of either propylene or isobutene. The second stream 312 is passed to a first oligomerization reactor 320 operated at reaction conditions for a conversion of less than 70% of the olefins to heavier hydrocarbons, and to generate a first oligomerization effluent stream 322. The first oligomerization effluent stream 322 is cooled to generate a cooled effluent stream 324. A first portion 326 of the cooled effluent stream is passed to the first oligomerization reactor 320, and a second portion 328 of the cooled effluent stream is passed to a flash unit 330 to generate a flash vapor stream 332 and a flash liquid stream 334.

The flash liquid stream 334 comprises olefinic distillate. A first portion 336 of the flash vapor stream is passed to the first oligomerization reactor 320, and a second portion 338 is passed to a second oligomerization reactor 340 to generate a second oligomerization effluent stream 342.

The flash liquid stream 334 is passed to a flash liquid stripper 350 to generate a flash liquid stripper overhead stream 352 and a flash liquid stripper bottoms stream 354. The flash liquid overhead stream comprised C9− hydrocarbons, and is directed to the second oligomerization reactor 340 for further growth of the hydrocarbons. The flash liquid bottoms stream comprises C10+ distillate hydrocarbons. This removes heavier oligomers from the second oligomerization reactor feed for control of the molecular weight and distillation 90% point of the distillate. This can also reduce potential catalyst deactivation by heavy distillate components by greatly lowering the distillate concentration in each reactor.

The second oligomerization effluent stream 342 is passed to a stabilizer 360 to generate a stabilizer overhead stream 362 comprising light paraffins and olefins, and a stabilizer bottoms stream 364. The stabilizer bottoms stream 364 is passed to a distillate stripper 370 to generate a distillate stripper overhead stream 372 and a distillate stripper bottoms stream 374. The overhead stream 372 comprises an olefinic gasoline that can be further processed, and the bottoms stream 374 comprises distillate.

The stabilizer overhead stream 362 can be passed to a complete saturation unit 380 to generate a paraffinic stream 382, and the paraffinic stream can be recycled to the dehydrogenation unit 310.

The heat generated by the reaction will cause the temperature of the reactor to arise. The temperature rise of the reactors can be limited by allowing for recycle of the heavy hydrocarbons generated in the effluent stream. In one case the temperature rise can be more effectively managed, or limited, by recycling or quenching with the effluent from the first reactor. The temperature can be further controlled with flashing the effluent. The flashed effluent will generate a cooler liquid that is lean in light olefins and will provide quenching and dilution of the feed to the first reactor. The flash vapor is condensed and passed to the second reactor. The recycle fluid will also contain higher concentrations of C6+ hydrocarbons and permit the operation of the reactors at lower pressures.

In another embodiment, the flash liquid stripper 350 is combined with the distillate stripper 370 into a common tower and at least a portion $C_9-$ hydrocarbons in streams 372 and 352 are recycled to the $2^{nd}$ oligomerization reactor for further hydrocarbon growth. In a further embodiment, olefinic distillate from strippers 350 and 370 are saturated in a complete saturation unit.

Table 3a,b shows the material balances of the configuration of FIG. 4 per 100 kg/hr of feed stream 320. The first oligomerization reactor, 320, is operated at 42% conversion with 138 kg/hr of recycle and 67% overall conversion. The second reactor, 340, is operated at 85% conversion with only 18 kg/hr of effluent recycle, for an overall conversion of 95% of the olefin in stream 312.Aa To maximize distillate selectivity and yield, the reactor 320 effluent is flashed to generate a distillate-lean vapor stream 322 and a distillate-rich flash liquid stream 354. The flash liquid is then stripped in stripper 350 to recover olefinic $C_6$-$C_9$ olefins and olefinic distillate 354 is withdrawn. In this table the olefinic $C_6$-$C_9$ stripper overhead 322 are recycled to increase distillate yield but these olefins can alternatively be routed to gasoline production. By operating the first oligomerization reactor at lower (42%) $C_3=$ conversion and removing the distillate produced therein it is possible to control the distillation 90% point at high overall $C_3=$ conversion (95% across both reactors) and increase the concentration of $C_3=$ and $C_6$-$C_9$ olefin reactants in both reactors to drive selectivity toward distillate.

TABLE 3a

2 Stage Adiabatic Oligomerization with Interstage Distillate Removal

| | Fresh feed comp. Kg/hr | Reactor 1 Recycle flows Kg/hr | Reactor 1 feed Kg/hr | Reactor 1 reaction Kg/hr | Reactor 1 effluent Kg/hr | Reactor 1 effluent flash + stripper vapor kg/hr | Reactor 1 effluent stripped distillate Kg/hr |
|---|---|---|---|---|---|---|---|
| C3= | 30 | 17.47 | 47.47 | −20.0 | 27.37 | 17.47 | |
| iC4= | 1 | 0.18 | 1.18 | −0.9 | 0.28 | 0.18 | |
| C5= | 0 | 0 | 0 | 0 | 0 | 0 | |
| C6= to C9= | 0 | 5.07 | 5.07 | 4.78 | 9.85 | 5.07 | |
| Aromatic (unreactive) | 0.15 | 0 | 0.15 | | 0.15 | 0 | |
| Dienes (reactive) | 0.05 | 0 | 0.05 | −0.05 | 0 | 0 | |
| Other (reactive) | 0.05 | 0 | 0.05 | −0.05 | 0 | 0 | |
| Other | 1.8 | 0 | 1.8 | | 1.8 | 0 | |
| C3 + iC4 | 66.95 | 118.15 | 185.1 | | 185.1 | 118.15 | |
| Oligomers | 0 | 1.13 | 1.13 | 16.32 | 17.45 | 2.76 | 14.69 |
| Total | 100 | 142.0 | 242.0 | 0 | 242.0 | 143.63 | 14.69 |

TABLE 3b

2 Stage Adiabatic Oligomerization with Interstage Distillate Removal

| | Reactor 2 feed comp. Kg/hr | Reactor 2 Recycle flows Kg/hr | Reactor 2 feed Kg/hr | Reactor 2 reaction Kg/hr | Reactor 2 effluent Kg/hr | Net Product Kg/hr |
|---|---|---|---|---|---|---|
| C3= | 9.9 | 0.32 | 10.22 | −8.4 | 1.82 | 1.5 |
| iC4= | 0.1 | 0.01 | 0.11 | −0.06 | 0.05 | 0.04 |
| C5= | 0 | 0.0 | 0 | 0 | 0.0 | 0.0 |
| C6= to C9= | 4.78 | 1.17 | 5.95 | 0.75 | 6.7 | 5.53 |
| Aromatic (unreactive) | 0.15 | 0.03 | 0.18 | | 0.18 | 0.15 |
| Dienes (reactive) | 0 | 0 | 0 | | 0 | 0 |
| Other (reactive) | 0 | 0 | 0 | | 0 | 0 |
| Other | 1.8 | 0.38 | 2.18 | | 2.18 | 1.8 |
| C3 + iC4 | 66.95 | 14.12 | 81.07 | | 81.07 | 66.95 |
| Oligomers | 1.63 | 1.98 | 3.61 | 7.71 | 11.31 | 24.03 |
| Total | 85.31 | 18.0 | 103.31 | 0 | 103.31 | 100.0 |

While the invention has been described with what are presently considered the preferred embodiments, it is to be understood that the invention is not limited to the disclosed embodiments, but it is intended to cover various modifications and equivalent arrangements included within the scope of the appended claims.

What is claimed is:

1. A process for managing heat release, conversion and selectivity in a dehydrogenation and oligomerization process, comprising:
    passing a first stream comprising propane or isobutane to a dehydrogenation reactor to generate a dehydrogenation stream comprising propylene or isobutene, operated to produce less than 50% conversion of the propane or isobutane;
    passing the dehydrogenation stream to a first oligomerization reactor, operated at conditions for a conversion of less than 70% of the propylene or isobutene in the dehydrogenation stream, to generate a first oligomerization effluent stream;
    passing a first portion of the first oligomerization effluent stream back to the first oligomerization reactor as a recycle stream wherein the first oligomerization effluent stream is sized to maintain a temperature in the first oligomerization reactor to less than 60° F.(33.3° C.);
    passing a second portion of the first oligomerization effluent stream to a second oligomerization reactor to generate a second oligomerization effluent stream; and
    passing the second oligomerization effluent stream to a distillate splitter.

2. The process of claim 1 wherein the first oligomerization reactor is operated to perform a conversion of at least 90% of propylene or isobutene to heavier hydrocarbons;
    passing the first oligomerization effluent stream to a stabilizer to generate a stabilizer overhead stream comprising C4 hydrocarbons and lighter gases, and a stabilizer bottoms stream comprising C6+ hydrocarbons;
    passing a first portion of the stabilizer bottoms stream to the second oligomerization reactor; and
    passing a second portion of the stabilizer bottoms stream to the first oligomerization reactor.

3. The process of claim 1 wherein the dehydrogenation reactor is operated to convert between 20 and 40% of the propane or isobutane in the first stream to propylene or isobutene.

4. The process of claim 1 further comprising:
    passing the second oligomerization effluent stream to a complete saturation unit to generate an effluent stream with reduced olefin content; and
    passing the effluent stream with reduced olefin content to the distillate splitter to generate an overhead stream for passing to a gasoline blending pool, and a distillate bottoms stream.

5. The process of claim 1 further comprising passing the second oligomerization effluent stream to a complete saturation unit to generate an effluent stream with reduced olefin content.

6. The process of claim 4 further comprising passing a portion of the distillate bottoms stream to the second oligomerization reactor.

7. The process of claim 1 further comprising:
    passing the dehydrogenation stream to an aromatics removal unit to generate an aromatics free dehydrogenation stream; and passing the aromatics free dehydrogenation stream to the first oligomerization reactor.

8. The process of claim 1 further comprising:
passing the dehydrogenation stream to a sulfur removal unit to generate a sulfur free dehydrogenation stream; and
passing the sulfur free dehydrogenation stream to the first oligomerization reactor.

9. A process for the production of distillate from light paraffins, comprising:
passing a first stream comprising light paraffins to a dehydrogenation zone to generate a second stream comprising light olefins;
passing the second stream to a first oligomerization reactor, operated at conditions for a conversion of less than 70% of the light olefins in the second stream, to generate a third stream comprising oligomers;
cooling the third stream to generate a cooled third stream;
passing a first portion of the cooled third stream to the first oligomerization reactor,
operated at reaction conditions sufficient to achieve oligomerization of the light olefins to less than 70% wherein the first portion of the cooled third stream is sized to maintain a temperature in the first oligomerization reactor to less than 60° F.(33.3° C.);
passing a second portion of the cooled third stream to a second oligomerization reactor to generate a distillate process stream, operated at reaction conditions sufficient to achieve oligomerization of the light olefin to at least 90%; and
recovering distillate from the distillate process stream.

10. The process of claim 9 wherein the first stream comprising light paraffins comprises propane or isobutane.

11. The process of claim 9 wherein the second stream comprising light olefins comprises propylene or isobutene.

12. The process of claim 9 further comprising:
passing the distillate process stream to a stabilizer to generate an overhead stream comprising C3 and lighter hydrocarbons, and a bottoms stream comprising distillate;
passing a first portion of the bottoms stream to the second oligomerization reactor; and
passing a second portion of the bottoms stream to a distillate splitter to generate a distillate splitter overhead comprising olefinic gasoline, and a distillate splitter bottoms stream comprising distillate.

13. The process of claim 12 further comprising:
passing the distillate splitter bottoms stream to a complete saturation unit to generate a saturated distillate bottoms stream; and
passing the saturated distillate bottoms stream to a stripper to generate a light ends overhead stream and a distillate product bottoms stream.

14. A process for controlling the heat of reaction in a light paraffins to distillate conversion process, comprising:
passing a first stream comprising a light paraffin to a dehydrogenation unit to generate a second stream comprising a light olefin;
passing the second stream comprising the light olefin to a first oligomerization reactor operated at reaction conditions for a conversion of less than 70% of the light olefin to heavier hydrocarbons to generate a first oligomerization effluent stream;
passing the first oligomerization effluent stream to a flash unit to generate a flash vapor stream and a flash liquid stream;
as a recycle stream wherein the first portion of the flash liquid stream comprising unconverted light olefin and C6-C9 olefins is sized to maintain a temperature in the first oligomerization reactor to less than 60° F.(33.3° C.);
passing a second portion of the flash liquid stream and the flash vapor stream to a second oligomerization reactor to generate a second oligomerization effluent stream;
passing the second oligomerization effluent stream to a stabilizer to generate a stabilizer overhead stream and a stabilizer bottoms stream; and
passing the stabilizer bottoms stream to a distillate stripper to generate an olefinic gasoline overhead and a distillate stream.

15. The process of claim 14 further comprising passing a portion of the stabilizer bottoms stream to the second oligomerization reactor.

16. The process of claim 14 further comprising passing a portion of the olefinic gasoline overhead to the second oligomerization reactor.

17. The process of claim 14 further comprising:
passing the second portion of the flash liquid stream to a flash liquid stripper to generate a flash liquid stripper overhead stream comprising C9− hydrocarbons and a flash liquid stripper bottoms stream comprising C10+ hydrocarbons; and
passing the flash liquid stripper overhead stream to the second oligomerization reactor.

18. A process for controlling the conversion of paraffins to distillate, comprising:
passing a first stream comprising propane or isobutane to a dehydrogenation unit to generate a second stream comprising propylene or isobutene;
passing the second stream to a first oligomerization reactor operated at reaction conditions for a conversion of less than 70% of the olefins to heavier hydrocarbons to generate a first oligomerization effluent stream;
cooling the first oligomerization effluent stream to generate a cooled first oligomerization effluent stream;
passing a first portion of the cooled first oligomerization effluent stream to the first oligomerization reactor as a recycle stream wherein the first portion of the cooled first oligomerization effluent stream is sized to maintain a temperature in the first oligomerization reactor to less than 60° F.(33.3° C.);
passing a second portion of the cooled first oligomerization effluent stream to a flash unit to generate a flash vapor stream and a flash liquid stream comprising olefinic distillate;
passing a first portion of the flash vapor stream to the first oligomerization reactor;
passing a second portion of the flash vapor stream to a second oligomerization reactor to generate a second oligomerization effluent stream;
passing the flash liquid stream to a flash liquid stripper to generate a flash liquid stripper overhead stream comprising C9− hydrocarbons and a flash liquid stripper bottoms stream comprising C10+ distillate hydrocarbons;
passing the flash liquid stripper overhead stream to the second oligomerization reactor;
passing the second oligomerization effluent stream to a stabilizer to generate a stabilizer overhead stream and a stabilizer bottoms stream; and passing the stabilizer bottoms stream to the distillate stripper to generate an olefinic gasoline overhead and a distillate stream.

\* \* \* \* \*